United States Patent [19]

Donachie

[11] Patent Number: 5,587,166
[45] Date of Patent: Dec. 24, 1996

[54] VACCINE AGAINST PASTEURELLA

[75] Inventor: William Donachie, East Calder, Scotland

[73] Assignee: British Technology Group Limited, London, England

[21] Appl. No.: 427,692

[22] Filed: Apr. 24, 1995

Related U.S. Application Data

[63] Continuation of Ser. No. 106,720, Aug. 16, 1993, abandoned, which is a continuation of Ser. No. 168,960, Mar. 16, 1988, abandoned.

[30] Foreign Application Priority Data

Mar. 24, 1987 [GB] United Kingdom ............... 8706944
Sep. 10, 1987 [GB] United Kingdom ............... 8721286

[51] Int. Cl.$^6$ ..................... A61K 39/02; A61K 39/102
[52] U.S. Cl. .................... 424/255.1; 424/234.1; 424/236.1; 424/278.1; 530/350
[58] Field of Search .................. 424/234.1, 236.1, 424/255.1, 278.1, 94.1; 530/350

[56] References Cited

U.S. PATENT DOCUMENTS

| | | | |
|---|---|---|---|
| 2,844,515 | 7/1958 | Sobotka et al. | 195/100 |
| 3,113,078 | 12/1963 | Neely | 195/96 |
| 4,346,074 | 8/1982 | Gilmour et al. | 424/203.1 |
| 4,681,761 | 7/1987 | Mietzner et al. | 424/92 |

FOREIGN PATENT DOCUMENTS

| | | |
|---|---|---|
| 20356A | 1/1981 | European Pat. Off. . |
| 36995A | 10/1981 | European Pat. Off. . |
| 213947A | 9/1984 | German Dem. Rep. . |
| 216954A | 1/1985 | German Dem. Rep. . |
| 2023420 | 1/1980 | United Kingdom . |
| 2029219 | 3/1980 | United Kingdom . |

OTHER PUBLICATIONS

Corbett et al "Effect of Iron Deprivation on Outer Membrane Proteins of *Pasteurella multocida*", Abstracts of 85th Annual Meeting of the American Society for Microbiology, 1985, pp. 1–13.
P. G. Squire et al., Infection and Immunity 45, 667–673 (1984).
N. Gilmour and W. Donachie in "Science and Quality Lamb Production", pub. Agricultural and Food Research Council, UK, 1986, pp. 22, 23 & 28.
E. Griffiths et al., FEMS Microbiology Letters 16, 95–99 (1983).
E. Griffiths et al., Infection and Immunity 47, 808–813 (1985).
H. Chart and E. Griffiths, Society for General Microbiology (UK), 101st Ordinary Meeting, Sheffield, UK 18–20 Sep. 1984, poster P8.
C. A. Bolin et al., Infection and Immunity 55 (5), 1239–1242 (May 1987).
P. Stevenson and E. Griffiths in "The Virulence of *Escherichia coli*", ed. M. Sussman, Society for General Microbiology (UK), Special Publication No., 13, Academic Press (1985), pp. 413 to 417.
J. J. Bullen Eur. J. Clin. Microbiol. 4, 537–539 (1985).
A. Norquist et al., FEMS Microbiol. Letters 4, 71–75 (1978).
S. E. H. West and P. F. Sparling, Infection and Immunity 47, 388–394 (1985).
C. V. Seiortino and R. A. Finkelstein, Infection and Immunity 42, 990–996 (1983).
T. Koga and T. Kawati, Microbiology and Immunology 30, 193–201 (1986).
M. J. Kluger and B. Rothenburg, Science 203, 374–377 (1979).
K.–D. Flossmann et al., Zeitschrift fuer Allgemeine Mikrobiologie 24, 231–237 (1984) with English Translation.
K.–D. Flossmann et al. Zentralblatt Bakt. Hyg. A 258, 80–93 (1984) with English Translation.
M. J. Corbett et al., Abstracts of the 85th Annual Meeting, American Society for Microbiology, Las Vegas, USA, Mar. 3–7 1985, Abstract K194, p. 204.
S.–P. Hu et al., Infection and Immunity 54, 804–810 (1986).
K.–D. Flossmann et al., J. Basic Microbiol. 25, 559–567 (1985).
M. J. Gentry et al., Amer. J. Vet. Res. 47, 1919–1923 (1981).
G. Manoussakis et al., Eur. J. Med. Chem. 22, 421–425 (1987).
G. H. Shand et al., Infection and Immunity, 48, 35–39 (1985).
M. R. W. Brown et al., FEMS Microbiology Letters 21, 113–117 (1984).
H. Anwar et al., FEMS Microbiology Letters 29, 225–230 (1985).
Y. Fukuda et al. "Vaccination of Yellowtail against Pseudotuberculosis" Fish Pathology 20 (2/3) 1985, pp. 421–425.

*Primary Examiner*—Christine M. Nucker
*Assistant Examiner*—Laurie Scheiner
*Attorney, Agent, or Firm*—Nixon & Vanderhye

[57] ABSTRACT

A vaccine against Pasteurella comprising a proteinaceous material isolated from Pasteurella grown under iron-restricted conditions, but not from Pasteurella grown under normal conditions in vitro, which reacts in an immunoblotting test against the serum of a convalescent sheep or cow which has recovered from an infection by Pasteurella of the same serotype, together with an adjuvant.

15 Claims, 6 Drawing Sheets

VACCINE AGAINST PASTEURELLA

This application is a continuation of application Ser. No. 08/106,720 filed Aug. 16, 1993 which is a continuation of application Ser. No. 07/168,960 filed Mar. 16th, 1988, now abandoned.

BACKGROUND OF THE INVENTION

1. Field of the invention

This invention relates to a vaccine against bacteria of the genus Pasteurella, especially *Pasteurella haemolytica*, which is the organism responsible for pasteurellosis in sheep and one of those responsible for pasteurellosis in cattle, and *Pasteurella multocida*, which is another responsible for pasteurellosis in cattle.

2. Description of prior art

Pasteurellosis is a common respiratory disease of sheep and cattle which may often lead to fatality, particularly in the case of young animals, and thus the prevention and control of this disease is of great importance to farmers engaged in the rearing of sheep and cattle. In sheep the disease appears as either a pneumonia or a septicaemic condition dependent upon the age of the infected animal and the strain of the infecting organism, whereas in cattle the disease is encountered primarily as a pneumonia in regions with temperate climates. Two biotypes of *P. haemolytica* have been identified, the A biotype generally associated with septicaemias in young lambs and pneumonias in older sheep, and the T biotype generally associated with septicaemias in adult sheep, and within these two biotypes fifteen different serotypes (eleven "A" and four "T" serotypes) have been identified. Serotype A2 is particularly important in relation to sheep and A1 in relation to cattle.

It has been a problem to improve the antigenicity of commercial vaccines against pasteurellosis. The sheep vaccines comprise various strains of *P. haemolytica*, representing the more important of the biotypes and subtypes thereof. Cattle vaccines also comprise *P. multocida*.

European Patent Specification 36995A (Norden Labs.) describes a live vaccine of *Pasteurella haemolytica* and *multocida*, attenuated to make them less pathogenic by culturing them in broth containing an acridinium compound.

In UK Patent Specification 2023420A (Hoechst UK) a vaccine against *Pasteurella haemolytica* contains antigens said to be associated with the capsule of the bacterium. An extract of such antigens is prepared by heating and centrifuging the culture and collecting the supernatant. The precipitated cells are sterilised and washed. Both the supernatant and the washed cells are included in the vaccine.

French Patent Specification 2182909A (Wellcome) or the corresponding UK Specification 1441098 describe a vaccine component prepared from *P. haemolytica* or *multocida* by extracting a whole cell structure, lysate, or cell-free culture medium with a lower alkanol or lower alkyl ketone or "salting out" with a salt such as ammonium sulphate to precipitate endotoxin. Endotoxin is a lipopolysaccharide component present in the capsule of the organism. The endotoxin-free supernatant re-treated with the solvent or salt (as before) at a high concentration, to precipitate the antigenic substance for use as a vaccine component.

Another attempt at improvement is described in U.S. Pat. No. 4,346,074, or its European equivalent 20356B (National Research Development Corporation) or its British equivalent 2029219A (Gilmour et al.). These patents relate to a vaccine comprising as essential components capsular extract, especially sodium salicylate extract, of the A1 serotype in combination with heat-killed cells of the A2 serotype. In the extraction process, the bacterial cells are centrifuged, shaken in sodium salicylate solution and then re-centrifuged and the supernatant concentrated by dialysis.

For a recent review of vaccination against pasteurellosis, see N. Gilmour and N. Donachie in "Science and Quality Lamb Production" (Agricultural and Food Research Council, UK, 1986) pages 22, 23 and 28.

Additional prior art is referred to after the "Summary of the invention", without which its context would not be clear.

SUMMARY OF THE INVENTION

It has now been found that when Pasteurella organisms are grown under iron-restriction conditions, that is to say conditions restricting the availability of iron to the organism to less than it requires for normal growth in vitro, extraction of the outer membrane or of whole cell lysate give rise to a different protein profile from that obtained under normal growth conditions in vitro, that such an extract is more immunogenic than a corresponding outer membrane extract of the organism grown under said normal growth conditions, and that this improved immunogenicity is associated with proteinaceous material produced under iron-restriction conditions but not under said normal growth conditions. This proteinaceous material and cellular material containing it have been found to be valuable in vaccinating animals against Pasteurella, especially *P. haemolytica*, at least of the same serotype. The novel proteinaceous material is novel in the sense that it is detectable when the organism is grown under iron-restriction conditions but not when it is grown under normal, i.e. iron-replete, conditions in vitro. It is immunogenic in the sense that it reacts in an immunoblotting test against the serum of a convalescent animal which has recovered from an infection by Pasteurella of the same serotype.

The novel proteinaceous material may comprise one or more individual molecules and may be a free protein or a bound protein such as a glycoprotein and the term "proteinaceous material", as used herein, is to be construed broadly as any material which will give rise to peptide band(s) upon gel electrophoresis of the outer membrane extract containing it. The novel proteinaceous material is conveniently referred to herein as an "iron-restriction protein" or "IRP".

According to an important aspect of the invention, therefore, there is provided an iron-restriction protein of Pasteurella, especially *P. haemolytica*, being a proteinaceous material present in (and isolatable from) Pasteurella grown under iron-restriction conditions, but not isolatable from Pasteurella grown under normal (non-iron-restricted) conditions in vitro and which reacts in an immunoblotting test against serum of a convalescent animal which has recovered from an infection by Pasteurella of the same serotype.

Inactivated whole cells of Pasteurella grown under iron-restriction conditions, including "bacterin", for the purpose of preparing a vaccine, are included within the invention.

The invention further provides a killed vaccine against Pasteurella, especially *P. haemolytica*, comprising an iron-restriction protein as defined above and an adjuvant.

Antibodies, especially monoclonal antibodies, including anti-idiotype antibodies are also within the invention.

In countries where such protection is permissible, especially the United States, Australia and New Zealand, the invention also provides a method of vaccinating an animal against Pasteurella, especially *P. haemolytica*, which comprises administering to an animal susceptible to infection by Pasteurella a prophylactically effective amount of a proteinaceous material or of a vaccine as defined above. The invention further includes a method of passive immunisation wherein antibodies to said proteinaceous material are administered to the animal.

ADDITIONAL DESCRIPTION OF PRIOR ART

It is known that the different bacterium *Escherichia coli* secretes proteins which appear in an outer membrane extract of *E. coli* grown under iron restriction conditions but not under normal, iron replete, conditions in vitro. Under iron-restriction conditions, the organism appears to switch on (de-repress) a gene, normally repressed, which expresses a protein in its outer membrane which assists in iron-scavenging. Put simply, when the bacterial cell is starved of its proper iron requirement it takes steps to try to increase its supply by making a protein which acts as a receptor for an iron scavenger (known as a "siderophore") such as enterochelin. Iron restriction conditions can be created artificially by adding a good iron chelator, such as alpha, alpha-bipyridyl (also called alpha, alpha-dipyridyl), to the cell growth medium, whereby the cell is stimulated to manufacture the iron receptor protein. See, for example, E. Griffiths et al., FEMS Microbiology letter 16, 95–99 (1983) and Infection and Immunity 47, 808–813 (1985). The introduction in the FEMS reference mentions some other organisms known to secrete enterochelin under iron-restricted conditions, including a Salmonella species which produces new outer membrane proteins. It is speculated in the FEMS reference that the outer membrane iron receptor proteins can act as "virulence factors" in the sense that they help a pathogenic bacterium acquire iron so that it would survive longer in the host and thereby prolong the infection. Pathogenic *E. coli* recovered from lethally infected guinea pigs were found to contain two iron restriction proteins as major components of the outer membrane extract. There is no suggestion, however, that other bacteria produce new outer membrane proteins (OMPs) in response to iron restriction or that such proteins would have any value as vaccine components.

According to C. A. Bolin et al., Infection and Immunity 55 (No. 5), 1239–1242 (May 1987) the role of iron-regulated OMPs of *E. coli* as protective antigens had not previously been determined. These authors report that passive immunisation with antibodies against iron-regulated OMPs protected turkeys against *E. coli* septicemia.

A review of methods of producing iron-restricted bacteria has been given by P. Stevenson and E. Griffiths in the Methodology Section of "The Virulence of Escherichia coli", Ed. M. Sussman, Society for General Microbiology Special Publication No. 13, Academic Press (1985), at pages 413 to 417.

A. Norqvist et al., FEMS Microbiol. Letters 4, 71–75 (1978) have reported that iron starvation of *Neisseria gonorrhoea* produces new protein bands by gel electrophoresis of an outer membrane extract.

U.S. Pat. No. 4,681,761 (Mietzner et al) issued Jul. 21, 1987 describes a major iron-regulated protein of *N. gonorrhoeae* and its use as a vaccine component. Its molecular weight is about 37 KDal. and it is produced by the action of the cationic detergent cetyl trimethylammonium bromide to selectively solubilise the IRP from the gonococcal membranes.

When *Pasteurella multocida* was passaged many times (up to 200) in an iron-deficient medium, it was reported to have decreased virulence (sic), as measured by the $LD_{50}$ in mice, and in the one case tested, a decrease of immunogenicity, see K.-D. Flossmann et al., Zeitschrift für Allgemeine Mikrobiologie 24, 231–237 (1984). This reference appears therefore to provide a negative teaching in relation to the present invention. In any case, the invention is not concerned with attenuation by repeated passaging.

M. J. Gentry et al., Amer. J. Vet. Res. 47, 1919–1923 (1986) studied the production of cytotoxin by *P. haemolytica* A1 in various media containing iron-containing and iron-binding compounds and concluded that a certain minimum concentration of iron as well as the presence of a suitable carrier molecule (siderophore) might be critical for the efficient production of cytotoxin by *P. haemolytica*.

G. H. Shand et al., Infection and Immunity 48, 35–39 (1985) grew some gram-negative bacteria isolated from human urine under iron-sufficient and iron-restricted conditions, extracted outer membrane proteins (OMPs) and compared their profiles by gel electrophoresis. Some high molecular weight OMPs were present only when iron-restricted conditions had been used. They were weakly immunogenic when immunoblotted against patients' serum. For two of the organisms, *Klebsiella pneumoniae* and *Proteus mirabeis*, these OMPs unique to iron-restriction conditions were also found in the same bacteria allowed to grow in the urine of patients suffering from urinary tract infections. H. Anwar et al., FEMS Microbiology Letters 29, 225–230 (1985) showed that when *Pseudomonas aeruginosa* is grown under iron-depleted conditions at least six high molecular weight proteins are found in the OMP profile which are not ordinarily present. A patient suffering from burns and consequently acute infection by *P. aeruginosa* produced antibodies to OMPs including one of these iron-restricted membrane proteins. The paper says that if these findings are confirmed by further investigations, they may have importance in the design of protective protein vaccines and immunotherapy of burns patients infected by *P. aeruginosa*.

BRIEF DESCRIPTION OF THE ACCOMPANYING DRAWINGS

DESCRIPTION OF THE PREFERRED EMBODIMENTS

The invention is applicable to *P. haemolytica* organisms of biotype A or T, but biotype A is the more important epidemiologically. Within biotype A, serotype A2 is the most important in the vaccination of sheep and A1 in the vaccination of cattle. At present it is proposed to formulate the vaccine for homologous serotype use, i.e. an IRP derived from serotype A2 would be used to protect against infection by A2. It is confidently believed that within a given serotype an IRP derived from one strain will protect against infection by another strain. Thus, the invention includes a polyvalent vaccine containing IRPs from all the pathologically important Pasteurella Serotypes. For sheep this includes at least serotype A2 and preferably also at least A1, A6, A7 and A9. For cattle it includes at least serotype A1 and preferably also at least A2 and *P. multocida*.

The major IRP for *P. haemolytica* serotype A2 has a molecular weight of about 70,000 Daltons, as determined by gel electrophoresis. The molecular weight of the major IRP for other A serotypes of *P. haemolytica* and of *P. multocida* appears to be of the same order.

Another IRP has a molecular weight of about 30 to 35 kiloDaltons and is hereinafter referred to for brevity as "the 35 kDal protein". There are minor IRPs of other molecular weights included within the invention.

The essential requirement for the vaccine is that it contains at least one IRP of a Pasteurella organism. The IRP can be provided in many different formulations. For example, a whole cell vaccine can be formulated in which the cells of Pasteurella grown under iron-restriction conditions are killed by treatment with formalin (aqueous formaldehyde) or heat, for example at 60° C. for 20 minutes, or (by way of precaution) both methods. Particularly preferred is a bacterin preparation. (Bacterins are formalin-killed whole cells together with associated toxoids). Alternatively, any method of extraction by which outer membrane proteins are recovered can be used. One simple method is to extract cell envelopes which contain the outer membrane. These envelopes can be recovered by sonicating the cells. A preferred method of extraction is capsular extraction, which extracts the capsule of the organism including the outer membrane. One useful method of capsular extraction is that in which sodium salicylate is used: see U.S. Pat. No. 4,346,074 or European Patent 20356B mentioned above.

Figure 1:
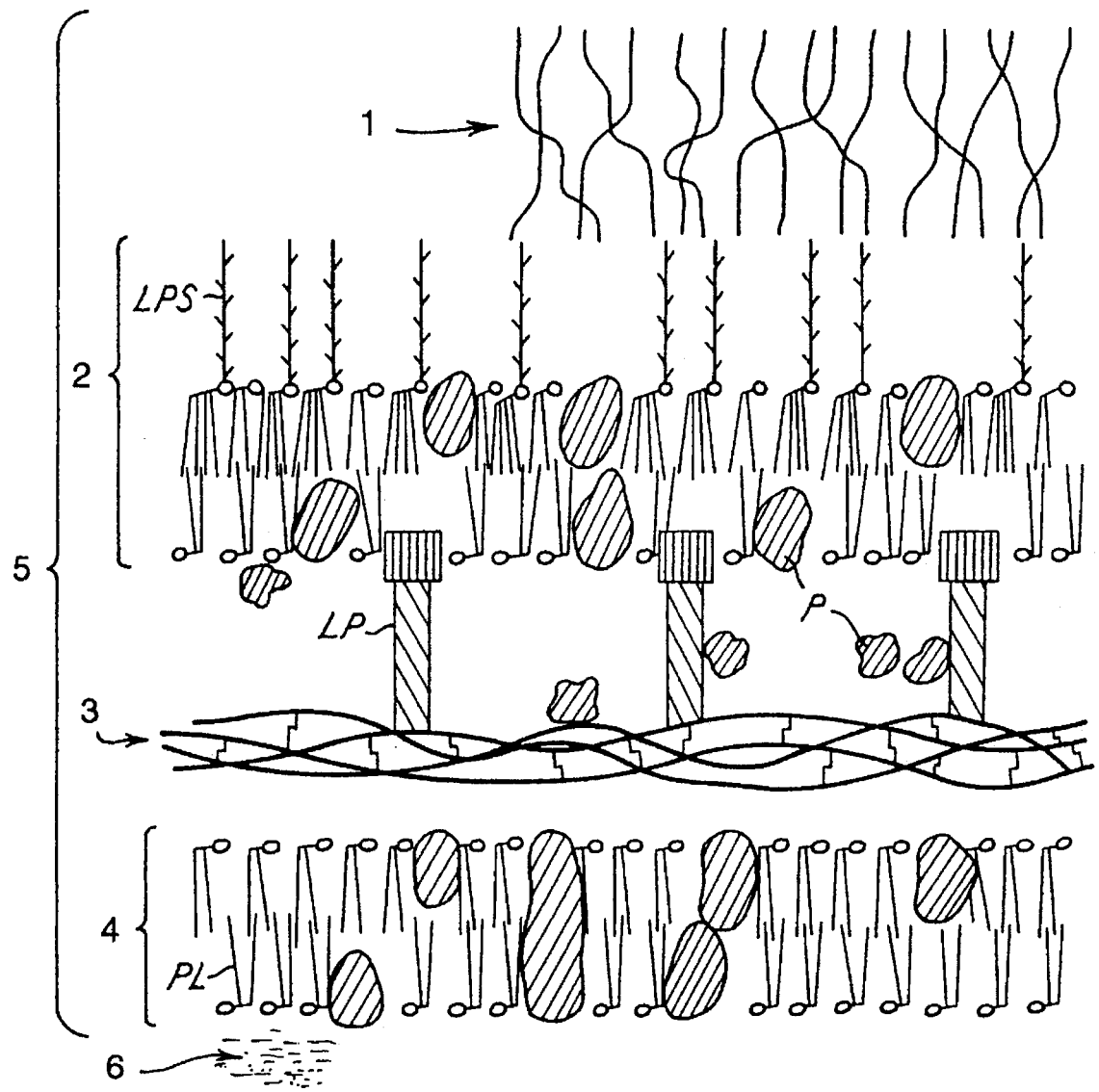
FIG. 1 is a section through the cell wall structure of *P. haemolytica* showing the outer membrane.

By way of explanation of the terminology used to describe the Pasteurella organism, see FIG. 1 of the accompanying drawings, showing a schematic cross-section through the cell wall of the organism. Referring to the drawing:
"1" indicates the polysaccharide capsule;
"2" indicates the outer membrane incorporating lipopolysaccharide ("LPS");
"3" indicates the layer of rigid peptidoglycans joined to the outer membrane through lipoprotein ("LP") and protein ("P");
"4" indicates the inner membrane incorporating phospholipid ("PL");
"5" indicates the envelope;
"6" indicates the cytoplasm.

A "capsular extract" will in practice contain more than the capsule 1. Thus, for example a sodium salicylate extract (SSE) extracts the capsule 1, outer membrane 2 and peptidoglycan layer 3.

It is, of course, possible to isolate the IRP and use it as such, for example by preparing a monoclonal antibody (MCA) to it, by conventional hybridoma technology, e.g. using mouse spleen mouse myeloma cell fusion, and subsequently using the MCA (immobilised on a column) to isolate the IRP from cellular extracts, and then recovering the IRP from the column.

Antibodies can also be raised against the monoclonal or polyclonal antibodies to the IRP and such raised antibodies are known as anti-idiotype antibodies and can themselves be monoclonal or polyclonal. The anti-idiotype antibodies are selected to have immunogenic properties similar to those of one or more of the original IRPs.

In formulating the vaccine, the proteinaceous material can be combined with any of the usual adjuvants in veterinary vaccines, typically those based on aluminium compounds. The aluminium hydroxide gel adjuvant "Alhydrogel" believed to be a Registered Trade Mark in some countries) is especially suitable. Preferably antigenic material is absorbed on to "Alhydrogel" and the resultant suspension optionally emulsified with a suitable oil, such as "Bayol F" preferably containing 10% "Arlacel A". The words "Bayol" and "Arlacel" are believed to be Registered Trade Marks. The vaccine can also include other components, for example a preservative.

The concentration of antigenic material in the vaccine may be varied as desired, for instance, in accordance with the dose rate of the vaccine, and in this respect the normal dose used is generally about 1–2 ml. Generally each dose of vaccine comprises 0.1 to 20 mg of antigenic material, especially from 0.5 mg up to 10 mg, e.g. about 5 mg, of antigenic material of each serotype included within the vaccine.

For prevention and control of pasteurellosis, e.g. for use in agricultural animal husbandry, the vaccines of the invention are administered to adult or juvenile animals, e.g. sheep or cattle, usually in the form of a subcutaneous injection. The animals may be vaccinated soon after birth to provide the animals with protection against pasteurellosis at an early stage in their lives. Also, vaccination may be carried out at particular periods of the year to provide protection against customary seasonal outbreaks of pasteurellosis. For example sheep flocks may be vaccinated in late spring or thereabouts with vaccines according to the invention comprising *P. haemolytica* A serotype antigenic material to provide protection against the outbreaks of pneumonic pasteurellosis which customarily occur in sheep flocks during the summer. Pregnant ewes can also be vaccinated.

Passive immunisation by antibodies to IRPs is also possible, particularly when an outbreak of disease occurs or is expected.

The invention further provides a process of preparing a vaccine component which consists of or includes an IRP, the process comprising growing the Pasteurella in a nutrient medium depleted in available iron, whereby the bacteria grow at a slower rate than normal, and optionally inactivating the bacteria or extracting from the cells material comprising outer membrane proteins.

The 70 kDal protein can be isolated from whole cell lysates or from outer membrane extracts. The 35 kDal protein has so far been isolated only from whole cells, but it would be possible to isolate it from an appropriate extract. It would also be possible to prepare these proteins by a recombinant DNA method, using monoclonal antibodies to detect their translation from mRNA, and thereby to identify cDNA clones. The invention includes these proteins per se, howsoever prepared or synthesised, chemically or biotechnologically, alone or fused with, conjugated to or complexed to other compatible proteins, and howsoever isolated, but preferably so as to be free from association with live cellular material.

The cells can be grown in any medium appropriate to the normal growth of the Pasteurella but which has been made iron-deficient. Examples of such normal growth media are broths based on meat digests such as GIBCO No. 2, OXOID, Brain Heart Infusion or Trypticase-Soy Broth. To make the media iron-deficient any iron chelator or binder can be used, so long as it is compatible with growth of the Pasteurella bacteria in culture. Examples of suitable iron-chelators are alpha, alpha-bipyridyl of formula:

<chemical structure of alpha,alpha-bipyridyl> nitrilotriacetic acid of formula:

$$HOOC-CH_2-N(CH_2-COOH)-CH_2-COOH$$

certain ethylenediamine-acetic acid compounds such as diethylenetriaminepentaacetic acid (DETPA), of formula:

$$(HOOCCH_2)_2N-CH_2CH_2-N(CH_2COOH)-CH_2CH_2-N(CH_2COOH)_2$$

and desferrioxamine of formula:

$$NH_2(CH_2)_5N(OH)-C(O)(CH_2)_2C(O)NH(CH_2)_5N(OH)-C(O)(CH_2)_2C(O)NH(CH_2)_5N(OH)-C(O)CH_3$$

(and salts or derivatives of any of these compounds which do not interfere with their chelating action.) Desferrioxamine methanesulphonate is available commercially as "Desferal-"(believed to be a Registered Trade Mark) from Ciba-Geigy AG, as an antidote to iron poisoning.

Care must be taken, however, not to use a chelating agent which binds other elements essential to the survival of the bacteria in preference to iron. EDTA, for example, is unsuitable from this viewpoint. The currently preferred chelating agent is alpha, alpha-bipyridyl.

The proportions of chelating agent to be used must be carefully controlled. Too great a concentration leaves the bacteria so short of iron that they do not grow at all. An insufficient amount will allow merely normal growths. In general terms, the optimal rate of growth at which to aim is one in which there is multiplication of the bacterial culture to at least 100 times the initial concentration in 6 hours when it is incubated at 37° C. on a shaker. In the absence of an iron-restricting agent, a typical multiplication under these conditions would be about 1000 times. The optimal concentration of chelating agent can be readily found by simple trial based on these criteria. For alpha, alpha-bipyridyl it is between 80 and 200, preferably between 100 and 200 micromolar. For DEPTA it is about between 25 and 500, preferably 50 to 200 micromolar.

Of course any other means of depleting the iron can be employed, there being no necessity to use a chelating agent in the medium in which the bacteria are being grown. For example, the medium could be pre-treated to remove iron by an ion-exchanger, for example "Chelex 100" from Biorad, and a defined low concentration of iron added to the medium.

Another possibility is to use a natural bacterial growth medium which already contains iron-binding proteins. Thus, a mammalian serum such as horse serum, suitably diluted necessary, could be used.

The cells can be grown otherwise under the normal conditions applicable to Pasteurella, for example in air, without shaking, at a temperature of from 25 to 41° C., preferably about 37° C.

The invention is applicable to many different species of Pasteurella including *P. haemolytica, P. multocida, P. piscicida* and *P. anatipestifer*. The vaccine can be used for the prophylaxis of any of the diseases associated with Pasteurella, e.g. any of the following diseases caused by *P. haemolytica*: pneumonia in sheep, cattle, deer and goats, septicaemias in many species of animals; any of the following diseases caused by *P. multocida*: pneumonias in pigs and cattle; atrophic rhinitis pigs, fowl cholera in chickens, turkeys and ducks, encephalomyelitis in buffalo, and snuffles and pneumonias in small mammals such as hamsters, rabbits and mink; as well as diseases in ducks caused by *P. anatipestifer* and fish caused by *P. piscicida*. In each case an IRP of the homologous species and type would normally be used.

The following Examples illustrate the invention.

EXAMPLE 1

Preparation of sodium salicylate extracts

P. haemolytica A2 was grown in stationary culture for 6 hours at 37° C. in GIBCO Nutrient Broth No. 2 (a trypsin digest of ox heart), with and without the addition of alpha, alpha-bipyridyl to a concentration of 150 micromolar. The final concentration of cells was about $10^9$ cells/ml in the case of normal growth and $10^7$ cells/ml in the case of iron restricted growth in the medium containing alpha, alpha-bipyridyl. The cells were harvested by centrifugation and the supernatant liquid was discarded. The cells were washed in phosphate-buffered saline, pH 7.4 ("PBS"), resuspended in one tenth of the volume of 1M aqueous sodium salicylate, shaken vigorously for 3 hours at 37° C., centrifuged and the cellular debris removed. The resultant sodium salicylate extract ("SSE") was concentrated by ultrafiltration through an exclusion membrane which allowed low molecular weight material (of m. w. 100,000 Daltons or less) to pass through. At this stage the IRP was in the form of aggregates. which were retained by the membrane. The retained material was concentrated tenfold, e.g. from 300 ml to 30 ml. It was then dialysed against PBS and then against distilled water at 4° C. The product was freeze-dried to a white fluffy solid.

Vaccine preparation and trial

Vaccines were prepared as follows. The freeze-dried SSE of *P. haemolytica* grown with and without iron-restriction, prepared as above, was homogenised with an equal part by weight of "Alhydrogel" adjuvant and with distilled water to a concentration of 2.5 mg SSE/ml of vaccine. Three week old specific pathogen-free (SPF) lambs were vaccinated on Day 0 and revaccinated on day 28, each time with a 1 ml dose of vaccine, then infected intratracheally and intranasally with parainfluenza virus type 3 (PI3) ($10^6$ TCID$_{50}$/ml) on day 35 and an aerosol of *P. haemolytica* A2 strain×205A (approx $4\times10^7$ cfu/litre) on day 42. Other three-week old SPF lambs were used as unvaccinated controls. (PI3 is a well-known inducer of *P. haemolytica* experimentally).

The lambs were observed for 6 days (days 43–48) after exposure to the *P. haemolytica* aerosol and clinical scores of the degree of illness suffered were recorded. 13 of the 28 lambs, six in the SSE without iron-restriction group and seven unvaccinated, died or were killed because of severe illness within 6 days of challenge. The remaining lambs were killed in random order on day 49 and the lungs of all lambs were examined.

The results obtained are given below in Table 1 below. As can be seen, the results were excellent, a remarkable degree of protection being conferred on the lambs by the vaccine of the invention.

| Group | No. lambs. | No. dead lambs | No. lambs with lung lesions | No. lambs with infected lungs |
|---|---|---|---|---|
| SSE IRP (according to the invention) | 8 | 0 | 0 | 0 |
| SSE (Comparative) | 13 | 6 | 9 | 8 |
| Unvaccinated controls. | 7 | 7 | 7 | 7 |

EXAMPLE 2

The effect of iron restriction on the antigenicity of *P. haemolytica* A2 was examined by SOS-PAGE and immunoblotting. Cells of *P. haemolytica* (Strain x 205) were grown in GIBCO nutrient broth No.2 (Nb) containing "Desferal", in Nb containing alpha, alpha-bipyridyl (AABP) and in 80% horse serum/20% PBS, as described in Example 1. Envelopes (cell wall material containing outer membrane proteins) were prepared from the bacterial cells by resuspending them in distilled water and sonicating them for 6×30 seconds in a MSE Sonicator. The unbroken cells were removed by centrifugation at 3000 g for 20 minutes. The supernatant was centrifuged at 40,000 g for 45 minutes to pellet the envelopes, which were then washed twice in distilled water.

For comparative purposes, cells of the same *P. haemolytica* A2 strain grown "in vivo" were obtained from the pleural fluid of specific pathogen free (SPF) lambs which had been exposed to an aerosol of the same A2 strain and had developed pneumonia with pleural exudate. The pleural fluid was removed from the opened thorax with a sterile 25 ml pipette and between 100 and 1000 ml of fluid could be obtained. This fluid was then centrifuged at 1000 g for 10 minutes to remove red blood cells and other unwanted particles in the fluid. Bacterial cells were pelleted by centrifugation at 3000 g for 20 minutes. These cells were washed 3 times in isotonic saline and stored at −20° C. The various preparations were subjected to SOS-PAGE using a 3% acrylamide stacking gel and a 12½% acrylamide separating gel. The gel was stained with Coomassie Blue dye.

Figure 2:
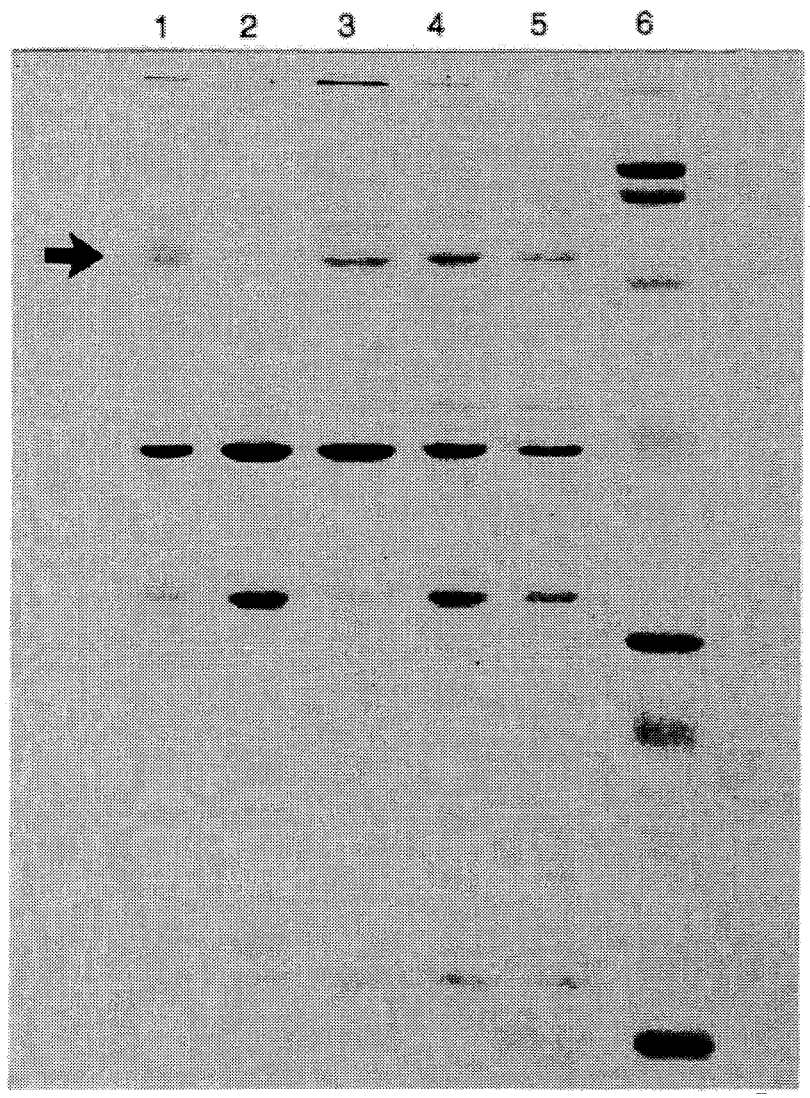
FIG. 2 shows stained gel electrophoresis profiles of proteins obtained from outer membrane extracts of *P. haemolytica* serotype A2 grown under normal and iron-restricted conditions.

Referring now to FIG. 2 of the drawings which shows the gel, the arrow indicates the novel IRP of the invention. The tracks are as follows:
1. A2 cell envelopes grown in vivo.
2. A2 cell envelopes grown in nutrient broth (comparative).
3. A2 cell envelopes grown in 80% horse serum.
4. A2 cell envelopes grown in nutrient broth+AABP (200 micromolar).
5. A2 cell envelopes grown in nutrient broth+"Desferal" (2 mg/ml).
6. Molecular weight markers as listed below.

The molecular weight markers were as follows:

| Number | Component | Mol wt |
|---|---|---|
| 1 | Beta-galactosidase | 116,000 |
| 2 | Phosphorylase b | 97,000 |
| 3 | Ovotransferrin | 76–80,000 (broad band) |
| 4 | Albumin | 66,250 |
| 5 | Ovalbumin | 45,000 |
| 6 | Chymotrypsinogen A | 25,700 |
| 7 | Myoglobin | 17,200 |
| 8 | Cytochrome C | 12,300 |

It will be seen that the IRP appears in tracks 3, 4 and 5, where the cells were grown under iron restriction conditions and that there is a faint band in track 1. (Note: the band at about 30,000 Daltons in tracks 1 to 5 is, of course, not the "35 kDal" IRP referred to above and in Examples 5 and 6).

For the immunoblotting, convalescent sera were obtained from SPF lambs which had been exposed to two aerosols of the same A2 strain, with a 4 week interval between these challenges. The sera were taken one week after the second exposure. They were shown to have high titres of antibody against *P. haemolytica* A2 in a specific enzyme-linked immunosorbent assay (ELISA).

Figure 3:
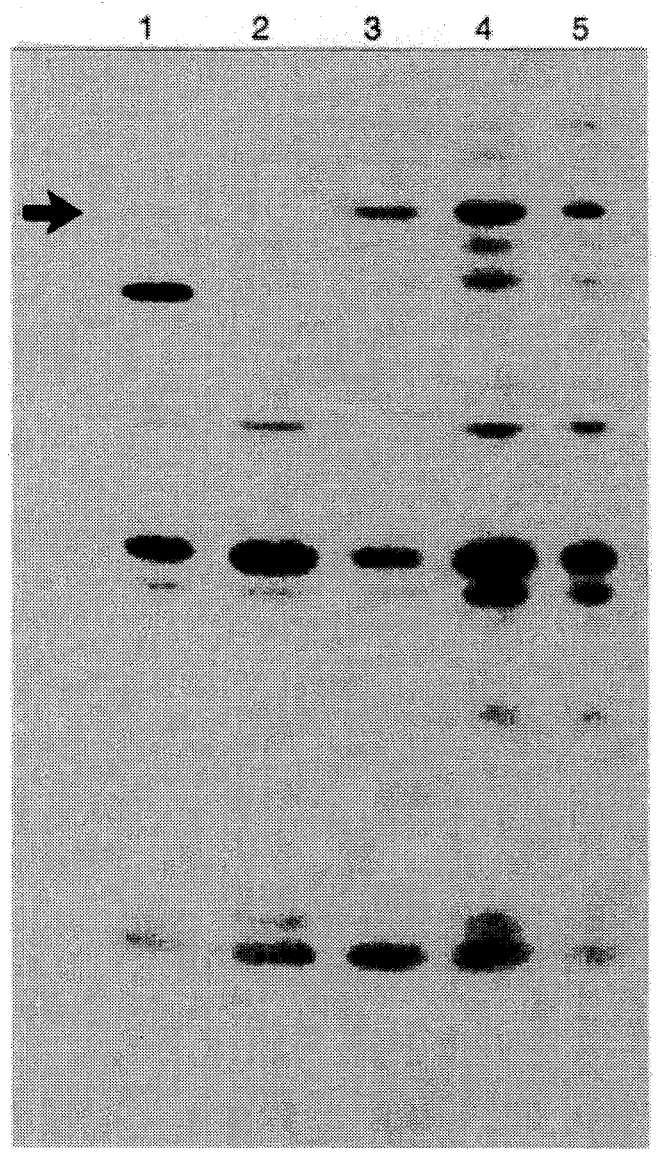
FIG. 3 shows an immunoblot of *P. haemolytica* A2 proteins from a gel similar to FIG. 2 against serum from convalescent lambs infected with *P. haemolytica* A2.

The gel bands as above for FIG. 2 were transferred to a nitrocellulose membrane by electro-blotting. The nitro-cellulose membrane filter with the proteins bound thereto was cut into strips and allowed to react with the convalescent serum diluted 1 in 40 in blot wash buffer (PBS/TNEEN 80/EDTA/NaCl). The antigen-antibody interaction was detected by washing the strips in the buffer, soaking them In rabbit anti-sheep IgG labelled with $^{125}$I, washing in blot wash buffer and autoradiography. Referring now to FIG. 3 in which the tracks correspond with tracks 1–5 of FIG. 2, it will be seen that the IRP reacted positively in all the relevant tracks (1, 3, 4 and 5), but did not react in the comparative track 2. This indicates that the IRP is associated with the high antigenicity of the preparations of the invention.

EXAMPLE 3

Figure 4:
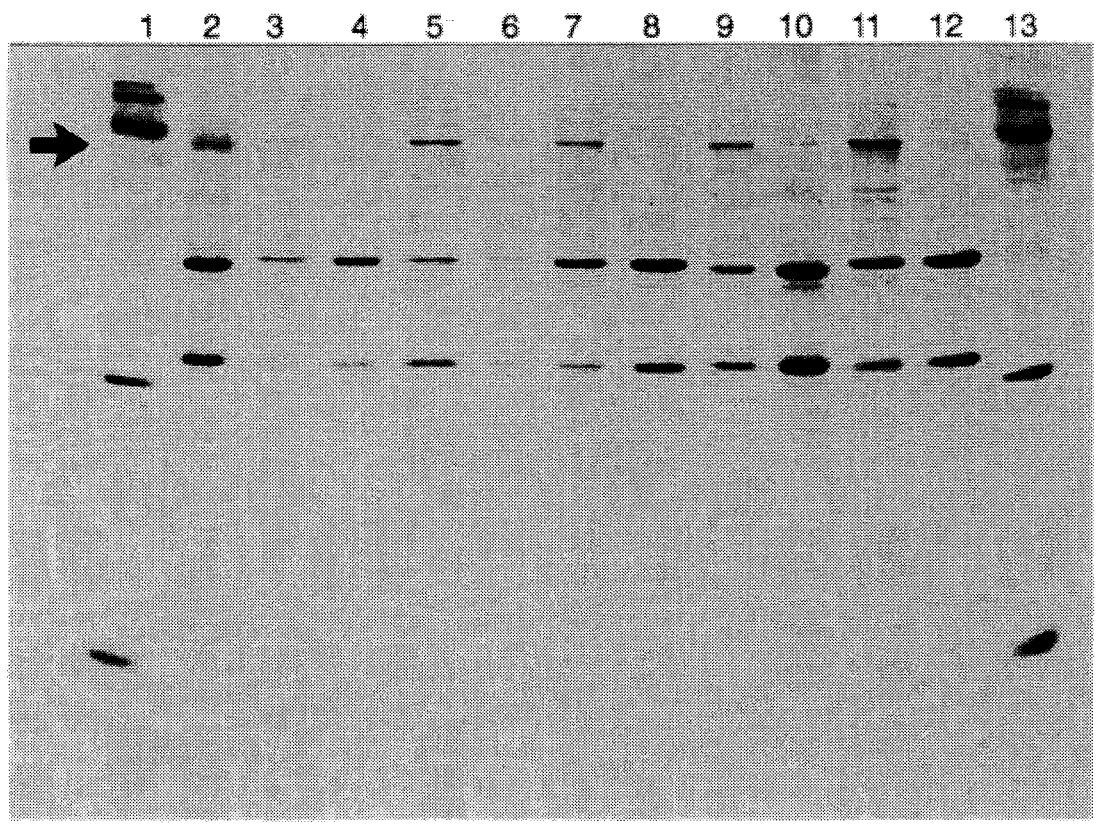
FIG. 4 shows stained gel electrophoresis profiles of proteins obtained from outer membrane extracts of five different serotypes of *P. haemolytica*.

Using the procedure of Example 2, cell envelopes were prepared from *P. haemolytica* serotypes A1, A2, A6, A7 and A9 grown in nutrient broth, with and without alpha, alpha-bipyridyl(AABP). An A2 "in vivo" sample prepared as in Example 2 was again included. SDS-PAGE was carried out as in Example 2 to produce the gels shown in FIG. 4. The arrow indicates the major IRP band and the identification of the tracks is as follows:
1. Molecular weight markers as in Example 2.
2. A2 cell envelopes grown in vivo.
3. A9 cell envelopes grown in nutrient broth+AABP.
4. A9 cell envelopes grown in nutrient broth.
5. A7 cell envelopes grown in nutrient broth+AABP.
6. A7 cell envelopes grown in nutrient broth.
7. A6 cell envelopes grown in nutrient broth+AABP.
8. A6 cell envelopes grown in nutrient broth.
9. A2 cell envelopes grown in nutrient broth+AABP.
10. A2 cell envelopes grown in nutrient broth.
11. A1 cell envelopes grown in nutrient broth+AABP.
12. A1 cell envelopes grown in nutrient broth.
13. Molecular weight markers as in Example 2.

It will be seen that the molecular weight of the IRP is about the same in all the tracks representing cells grown under iron-restriction (tracks 3, 5, 7, 9 and 11) and also occurs in the "in vivo" A2 track 2.

Immunoblotting by the procedure of Example 2 but against convalescent serum of only the A2 serotype showed that only the A2 IRP reacted. This suggests that although the major IRPs have about the same molecular weight, they are serotype-specific.

EXAMPLE 4

The Example shows that IRPs are also produced by two *P. haemolytica* T serotypes.

Cell envelopes were prepared by the procedure of Example 2, from *P. haemolytica* T10 grown in 80% horse serum/20% PBS and in GIBCO nutrient broth No.2 (Nb) containing 2 mg/ml. "Desfetal" and from *P. haemolytica* T15 grown in 80% horse serum/20% PBS and in Nb containing AABP at 200 μM concentration. SDS-PAGE and staining were carried out as in Example 2 along with an A2 cell envelope preparation from Example 2. The T type samples displayed new or significantly denser bands in the region of 70 KDal molecular weight.

EXAMPLE 5

*Pasteurella multocida*, type A strain was grown in 50 ml nutrient broth, with and without 150 micromolar AABP, for 18 h at 37° C. The cells were harvested by centrifugation, washed once in PBS, pH 7.4, resuspended in distilled water and sonicated. Whole cells remaining after sonication were pelleted by centrifugation at 2,800 g and the supernatant centrifuged at 40,000 g to pellet cell envelopes. The cell envelopes were adjusted to 1 mg/ml protein and separated by SDS-PAGE in 12.5% acrylamide-resolving gels. After electrophoresis, one portion of the gel was stained with Coomassie blue while the other portion was Western-blotted to transfer proteins to nitrocellulose paper. The blotted material was reacted with sera from mice which had capsules containing live *P. multocida* type A implanted in their peritoneal cavities in order to stimulate antibodies to in vivo grown *P. multocida* cells.

Figure 5:
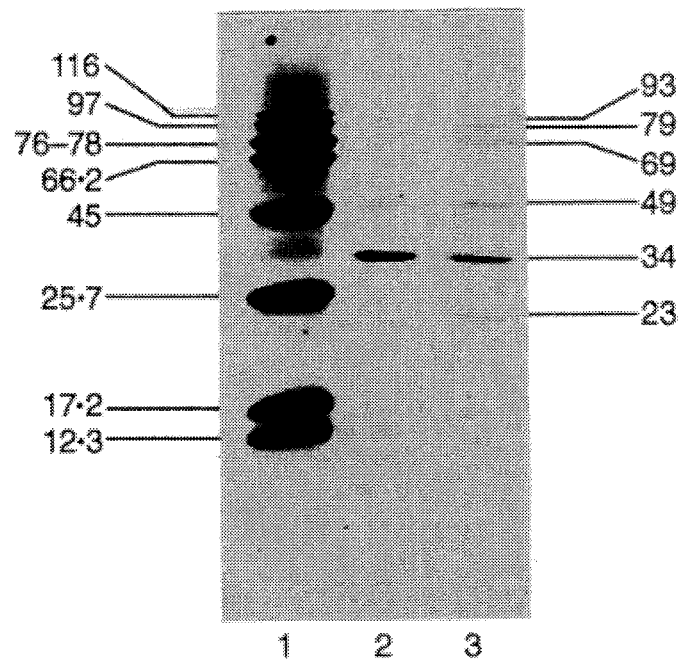
FIGS. 5 and 6 are analogous to FIGS. 2 and 3 respectively but relate to P. multocida.
Figure 6:
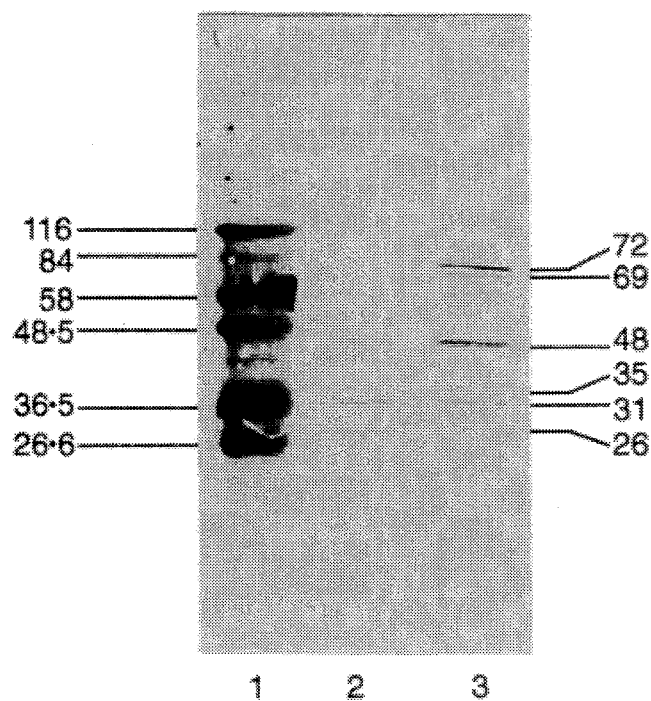

FIG. 5 shows the electrophoretic gels for molecular weight markers (as set out in Example 2) in track 1, the preparation from nutrient broth-grown *P. multocida* (grown without AABP) in track 2 and the preparation from *P. multocida* grown with AABP in track 3. Track 3 showed a weakly staining band in the 70 kDal region present in the track of AABP-grown cell envelopes, but not present to the same degree in that of the nutrient broth-grown cell envelopes. The immunoblot of the AABP-grown envelopes as shown in FIG. 6, with tracks 2 and 3 corresponding to 2 and 3 of FIG. 5, and different molecular weight markers in track 1, gave a strongly immuno-reacting doublet in the same molecular weight region, around 70 kDal, not present in that of the nutrient broth-grown envelopes. These are ascribed to IRPs. This is similar to the results obtained for *P. haemolytica* A2. A minor band, at around 35 kDal, is also unique to the immunoblot of AABP-grown envelopes, i.e. is not present in the nutrient broth-grown envelope profile. This is considered to be the minor IRP of the invention, which is described as having m.w. about 30 to 35 kDal.

EXAMPLE 6

This Example concerns the identification, extraction and antigenic analysis of the 35 kDal protein in *P. haemolytica* cells grown under iron restriction conditions.

Cells of *P. haemolytica* A2 (strain Y510) were grown GIBCO nutrient broth No.2 with and without the addition of AABP 150 micromolar). The cells were harvested by centrifugation and washed in PBS (pH 7.4) before use in vaccination.

Iodination of whole cells with radioactive iodine was carried out under conditions that favour iodination of surface proteins, i.e. low temperature, short reaction time and using intact log phase cells. Thus, one Pierce Iodobead (chloramine T immobilized on a solid phase), 1 ml of *P. haemolytica* cells and 2 milliCuries of iodine-125 were reacted for 5 minutes at room temperature, the liquid removed, 250 microlitres of 50 nanomolar 2-mercaptoethenol added and after waiting for 1 minute, 1% w/v potassium iodide solution and PBS were added. The resultant protein material was washed three times with PBS.

Whole cell lysates separated on SDS PAGE and stained for total protein with Coomassie blue showed a characteristic complex staining pattern that is similar in cells grown in high and low iron conditions. Autoradiography of iodinated cell proteins separated by SDS-PAGE reproducibly identifies a subset of some 20 proteins that are possibly associated with the cell surface.

The autoradiographic patterns of cells grown in conditions of iron sufficiency or restriction clearly differ in their banding patterns. Those grown in conditions of restricted iron exhibit additional bands at approximately 35, 70 and 100 kDal.

To purify these proteins for use in vaccination, whole cell lysates solubilised in 6M guanidine hydrochloride were fractionated at 30° C. by reversed phase HPLC. The column used was a Polypore PLRP-S-100A-5μ. The solvents were 0.1% Trifluoroacetic acid (TFA) in water, and 0.1% TFA in acetonitrile. A solvent gradient was used, starting with 99% of 0.1% TFA in water/1% of 0.1% TFA in acetonitrile for the first 5 minutes, then 95% of 0.1% TFA in water/5% of 0.1% TFA in acetonitrile for the next 5 minutes and a gradually decreasing proportion (95 to 5%) of 01.% TFA in water and increasing proportion of 0.1% TFA in acetonitrile for the remaining 160 minutes. The flow rate was 1 ml/minute. The chromatography was followed spectroscopically by reference to the UV absorption spectrum at 280 nm. Comparison of the A280 elution profiles demonstrated a clear difference in a single peak which was greatly enlarged in cells grown under iron-restricted conditions. Analysis of fractions corresponding to this peak by SDS PAGE and by two dimensional electrophoresis have shown that the major component of this peak is a 35 kDal protein with a small number of contaminating proteins. Significant amounts of this crudely purified 35 kDal protein have been isolated. Since the minor contaminating proteins in this material are quite distinct from the major 35 kDal protein in their molecular weights, the 35 kDal protein can be purified to substantial homogeneity by gel filtration.

Figure 7A:
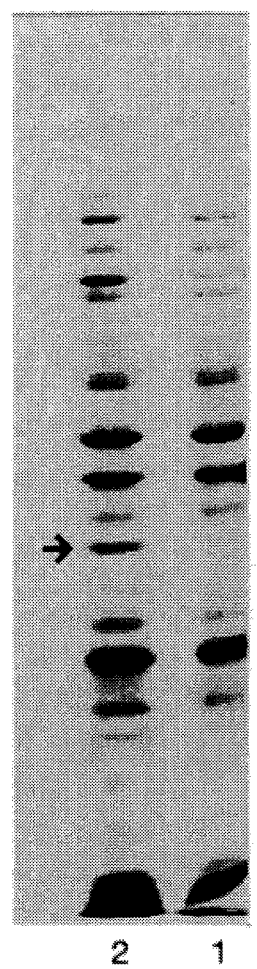
FIG. 7 is an immunoblot of an IRP of the invention against sera of convalescent, uninfected and vaccinated lambs.
Figure 7B:
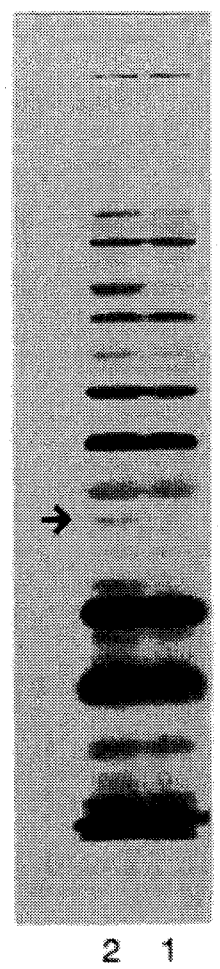

Western blotting provided evidence that the 35 kDal protein evokes an immune response in a natural infection in sheep, FIG. 7 of the drawings is a photograph of a gel (7a) and blot (7b) similar to that of FIGS. 2 and 3 and similarly obtained. Whole cell preparations grown in replete and in iron depleted media were separated by SDS-PAGE, transferred to nitrocellulose paper and probed with serum from SPF lambs as described in Example 2 except that the anti body-antigen interaction was detected by horseradish peroxidase (HRP) conjugated donkey anti-sheep IgG rather than by $125_I$ labelled pig anti-sheep IgG, FIG. 7a is a gel stained with Coomassie blue to visualise the antigens, while FIG. 7b is a Western blot of the gel of FIG. 7a with antisera from convalescent lambs. The 35 kDal band is arrowed in each Figure. The tracks are:

1. Whole cells of *P. haemolytica* A2 grown in nutrient broth.
2. Whole cells of *P. haemolytica* A2 grown in nutrient broth+AABP (150 micromolar).

I claim:

1. A vaccine comprising an effective amount of killed whole cells of *Pasteurella haemolytica* grown under iron-restriction conditions in vitro, together with an adjuvant.

2. The vaccine of claim 1 wherein said killed whole cells are in the form of a bacterin.

3. The vaccine of claim 1 wherein the said *Pasteurella haemolytica* is of serotype A2.

4. A vaccine comprising an effective mount of killed whole cells of *Pasteurella multocida* grown under iron-restriction conditions in vitro, other than conditions of attenuation by repeated passaging, together with an adjuvant.

5. The vaccine of claim 4 wherein said killed whole cells are in the form of a bacterin.

6. A vaccine comprising an effective mount of killed whole cells of *Pasteurella piscicida* grown under iron-restriction conditions in vitro, together with an adjuvant.

7. The vaccine of claim 6 wherein said killed whole cells are in the form of a bacterin.

8. A vaccine against Pasteurella which comprises an effective amount of a proteinaceous material selected from the group consisting of:

(a) isolated protein which is isolatable from *Pasteurella hacmolytica* grown under iron-restriction conditions in vitro but not from said *Pasteurella haemolytica* grown under normal conditions in vitro, which reacts in an immunoblotting test against serum of a convalescent animal which has recovered from an infection by said *Pasteurella haemolytica* of the same serotype; and (b) killed whole cells of *Pasteurella haemolytica* grown under iron-restriction conditions in vitro;

said proteinaceous material being formulated together with an adjuvant.

9. A vaccine against Pasteurella which comprises an effective mount of a proteinaceous material selected from the group consisting of:

(a) isolated protein which is isolatable from *Pasteurella piscicida* grown under iron-restriction conditions in vitro but not from said *Pasteurella piscicida* grown under normal conditions in vitro, which reacts in an immunoblotting test against serum of a convalescent animal which has recovered from an infection by said *Pasteurella piscicida* of the same serotype; and (b) killed whole cells of *Pasteurella piscicida* grown under iron-restriction conditions in vitro;

said proteinaceous material being formulated together with an adjuvant.

10. A method of prevention or control of pasteurellosis in sheep or cattle, which method comprises the step of administering to sheep or cattle a prophylactically effective amount of a proteinaceous material selected from the group consisting of (a) isolated protein which is isolatable from *Pasteurella haemolytica* grown under iron-restriction conditions in vitro but not from said *Pasteurella haemolytica* grown under normal conditions in vitro, which reacts in an immunoblotting test against serum of a convalescent animal which has recovered from an infection by said *Pasteurella haemolytica* of the same serotype;

(b) an extract comprising outer membrane proteins of a *Pasteurella haemolytica*, said extract containing a protein which is isolatable from said *Pasteurella haemolytica* grown under iron-restriction conditions in vitro but not from said *Pasteurella haemolytica* grown under normal conditions in vitro, and which reacts in an immunoblotting test against serum of a convalescent animal which has recovered from an infection by said *Pasteurella haomolytica* of the same serotype; and (c) killed whole cells of a *Pasteurella haemolytica* grown under iron-restriction conditions in vitro.

11. The method of claim 10 wherein said proteinaceous material is administered together with an adjuvant.

12. The method of claim 10 wherein said *Pasteurella haemolytica* is of serotype A2.

13. A method of prevention or control of pasteurellosis in sheep or cattle, which method comprises the step of administering to sheep or cattle a prophylactically effective mount of killed whole cells of *Pasteurella haemolytica* grown under iron-restriction conditions in vitro.

14. A method of prevention or control of pasteurellosis in cattle, which method comprises the step of administering to cattle a prophylactically effective amount of killed whole cells of *Pasteurella multocida* grown under iron-restriction conditions in vitro other than conditions of attenuation by repeated passaging.

15. A method of prevention or control of pasteurellosis in fish, which method comprises administering to fish a prophylactically effective mount of a proteinaceous material selected from the group consisting of (a) an isolated protein isolatable from *Pasteurella piscicida* grown under iron-restriction conditions in vitro but not from said Pasteurella grown under normal conditions in vitro and which resets in an immunoblotting test against serum of a convalescent fish which has recovered from an infection by said *Pasteurella piscicida* of the same serotype, and (b) killed whole cells of *Pasteurella piscicida* grown under iron-restriction conditions in vitro.

* * * * *

UNITED STATES PATENT AND TRADEMARK OFFICE
CERTIFICATE OF CORRECTION

PATENT NO. : 5,587,166
DATED : December 24, 1996
INVENTOR(S) : Donachie

It is certified that error appears in the above-identified patent and that said Letters Patent is hereby corrected as shown below:

On the title page, under item [56], Foriegn Patent Documents insert: 82/02491 dated 8/1982 PCT--.

On title page, under item [56] Other Publications, insert the following:

B. Lugtenberg et al., "Molecular architecture and functioning of the outer membrane...", Biochim. Biophys. Acta. 737, 51-115 (1983).

K.P. Snipes, "Virulence factors associated with avian strains of Pasteurella multocida", Ph.D. thesis, University of California, Davis (1985).

J.H. Crosa et al., "Outer membrane proteins induced under conditions of iron limitation in the marine fish pathogen..." Infection and Immunity 31, 223-227 (1981).

C.V. Sciortino et al., "Monoclonal antibodies to outer membrane antigens..." Infection & Immunity 49, 122-131 (1985).

S.P. Sigel et al., "Effect of iron limitation on growth, siderophore production...", J. Bacteriology 150, 148-155 (1982).

P.A. Sokol et al., "Characterization of antibody to the ferripyochelin-binding protein...", Infection & Immunity 51, 896-900 (1986).

R.C. Hedstron et al., "Antibody response of infected mice to outer membrane proteins...", Infection and Immunity 43, 49-53 (1984).

K.K. Grewal et al., "An inducible outer membrane protein...", FEBS Letters, 140, 27-30 (1982).

J.B. Neilands, "Microbial envelope proteins related to iron", Ann. Rev. Microbiol. 36, 285-309 (1982).
A.K. Bachawat et al., "Isolation and characterization of the outer membrane proteins...", J. Gen. Microbial. 133, 1751-1758 (1987).

UNITED STATES PATENT AND TRADEMARK OFFICE
CERTIFICATE OF CORRECTION

PATENT NO. : 5,587,166
DATED : December 24, 1996
INVENTOR(S) : Donachie

It is certified that error appears in the above-identified patent and that said Letters Patent is hereby corrected as shown below:

A.K. Bachawat et al., "Isolation and characterization of the outer membrane proteins...", J. Gen. Microbiol. 133, 1751-1758 (1987)

T. Aoki et al., "The outer membrane proteins of fish pathogens," FEMS Microbiol. Letters, 27, 299-305 (1985).

K. D. Flossmann et al., "Bedeutung von Eisen für die Ernährung von Pasteurellen und Salmonellen", Zeitschrift für Allg. Mikrobiol. 16, 217-219 (1976).

K.-D. Flossmann et al., "Einfluss von Eisen auf die Virulenz von Pasteurella multocida", Acta Bio. Med. German. 39, 327-334 (1980).

K.-D. Flossmann et al., "Wirkung parenteraler Eisengaben auf die experimentelle Infecktion mit Pasteurella multocida bei Maus und Schwein", Arch. exper. Vet. Med. Leipzig 37, 217-225 (1983).

Vineland Laboratories Inc., "Fowl cholera bacterin" (information leaflet), 2 pages, date unknown.

Maine Biological Laboratories Inc., "mbl Inactivac-FC3 Pasteurella multocida bacterin" (information leaflet), 1 page, date unknown.

Salsbury Laboratires, "Pasteurella multocida bacterin" (product label), date unknown (before Dec. 11, 1988).

Rhone-Merieux, "Avipastovax" (extract from brochure, pages 175-176), date unknown.

J.J. Bullen et al., "Abolition of Passive Immunity to Bacterial Infections by Iron", Nature 214, 515-516 (1967).

J.J. Bullen et al., "The Abolition of the Protective Effect of *Pasteurella septica* antiserum by Iron Compounds", Immunology 14, 889-898 (1968).

J.J. Bullen et al., "Bacterial Iron Metabolism and Immunity to *Pasteurella septica* and *Escherichia coli*, Nature 224, 380-382 (1969).

UNITED STATES PATENT AND TRADEMARK OFFICE
CERTIFICATE OF CORRECTION

PATENT NO. : 5,587,166
DATED : December 24, 1996
INVENTOR(S) : Donachie

It is certified that error appears in the above-identified patent and that said Letters Patent is hereby corrected as shown below:

M.J. Corbett et al., "Relationship of *Pasteurella multocida* Outer Membrane Proteins to Immunoprotection.", Abstracts of the Annual Meeting, Amer. Soc. Microbiol. Abstr. E47, page 84.

Column 7, line 63: after "diluted" insert --if,--.

Column 8, line 9: after "rhinitis" insert --in--.

Column 9, lines 21 and 46: change "SOS-PAGE" to --SDS-PAGE--.

Column 10, line 25: change "PBS/TNEEN" to --PBS/TWEEN--.

Column 11, line 8: change " "Desfetal" " to --"Desferal"--.

Column 13, lines 5, 12 and 32, and column 14, lines 26 and 37: change "mount" to --amount--.

Column 14, line 42: change "resets" to --reacts--.

Signed and Sealed this

Ninth Day of December, 1997

Attest:

BRUCE LEHMAN

Attesting Officer

Commissioner of Patents and Trademarks

(12) EX PARTE REEXAMINATION CERTIFICATE (6695th)
United States Patent
Donachie

(10) Number: US 5,587,166 C1
(45) Certificate Issued: Mar. 10, 2009

(54) VACCINE AGAINST PASTEURELLA

(75) Inventor: William Donachie, East Calder (GB)

(73) Assignee: National Research Development Corporation, London (GB)

Reexamination Request:
No. 90/007,964, Mar. 8, 2006
No. 90/008,762, Jul. 5, 2007

Reexamination Certificate for:
Patent No.: 5,587,166
Issued: Dec. 24, 1996
Appl. No.: 08/427,692
Filed: Apr. 24, 1995

Certificate of Correction issued Dec. 9, 1997.

Related U.S. Application Data

(63) Continuation of application No. 08/106,720, filed on Aug. 16, 1993, now abandoned, which is a continuation of application No. 07/168,960, filed on Mar. 16, 1988, now abandoned.

(30) Foreign Application Priority Data

Mar. 24, 1987 (GB) .............................................. 8706944
Sep. 10, 1987 (GB) .............................................. 8721286

(51) Int. Cl.
*C07K 16/12* (2006.01)
*A61K 39/102* (2006.01)

(52) U.S. Cl. ............... 424/255.1; 424/234.1; 424/236.1; 424/278.1; 530/350

(58) Field of Classification Search ........................ None
See application file for complete search history.

(56) References Cited

U.S. PATENT DOCUMENTS 4,346,074 A    8/1982   Gilmour et al.

OTHER PUBLICATIONS

Fukuda et al., "Vaccination of Yellowtail against Pseutuberculosis" Fish Pathology 20 (2/3) 1985, pp. 421–425.*
Corbett et al., Effect of Iron Deprivation on Outer Membrane Proteins of *Pasteurella multocida*, Abstracts of 85th Annual Meeting of the American Society for Microbiology, 1985, pp. 1–13.*
Kirby et al., "Receptor–Mediated Iron Acquisition from Transferrin in the the *Pasteurellaceae*", Haemophilus, Actionobacillus, and Pasteurella (1995) Plenum Press, New York, 115–127.
Shewen & Wilkie, "Vaccination of Calves with Culture Supernatant from *Pasteurella Haemolytico* A1 grown in Serum–Free Medium", Meeting Guide and Abstract Book: 1$^{st}$ International Veterinary Immunology Symposium, University of Guelph, Guelph, Ontario, Canada, Jul. 1–4, 1986, p. 127.
Babyut et al., "Interaction of Pasteurella haemolytica with Bovine Neutrophils: Identification and Partial Characterization of a Cytotoxin", Am J Vet Res 42, 1920–1926 (1981).

Blood & Studdert, Baillier's Comprehensive Veterinary Dictionary (1988), p. 90.
Bolin & Jensen, "Passive Immunization with Antibodies against Iron–Regulated Outer Membrane Protein Protects turkeys from *Escherichia coli* Septicemia", Infection and Immunity 55(5), 1239–1242 (1987).
Cameron & Bester, "Formulation of an effective *Pasteurella multocida* Vaccine for Sheep", Onderstepoort J. vet. Res. 51, 189–191 (1984).
Corbett et al., "Effect of Iron Deprivation on Outer Membrane Proteins of *Pasteurella multocida*", Abstracts of 85th Annual Meeting of the American Society for Microbiology, Las Vegas, USA, Mar. 3–7, 1985, Abstract K194, p. 204.
Flossman et al., "Beeinflussing von Virulenz und Immunogenitat bei *Pasteruella multocida* durch Eisen in vitro", Zeitschrift fur Mikrobiologie 24 (1984) 4, 231–237.
Gaunt et al., "Fowl Cholera: Immunization of Chickens with Potassium Thiocyanate (KSCN) Extract of *Pasteurella multocida* Serotype 3", Avian Diseases vol. 21 No. 4 (1974), 543–548.
Gentry et al., Cytotoxin (leukotoxin) production by *Pasteurella haemolytica*: Am J Vet Re. 47, 1919–1923 (1988).
Layton, "Efficacy of Broth–Grown *Pasteurella multocida* Bacterins in Ducklings", Avian Diseases vol. 28 No. 4 (1984), 1086–1095.
Shewen & Wilkie, "Evidence for the *Pasteurella haemolytica* cytotoxin as a product of actively growing bacteria", Am J Vet Res 46, 1212–1214, 91985).
Snipes, "Virulence factors associated with avian strains of *Pasteurella multocida*", Ph.D. thesis, University of California, Davis (1985) pp. iii–vii, 1–5, 19–25, 50–52, 108–116, 122, 123, 129, 130, 140–144, 161–165 and 182–189.
Squire et al., "Identification and Extraction of *Pasteurella haemolytica* Membrane Proteins", Infection and Immunity 45(3), 667–673.
Loan, R.W., et al.; "Proceedings of the 14$^{th}$ World Congress on Diseases of Cattle", Dublin, Ireland (1986); edited by P.J. Hartigan and M.L. Monaghan; Publisher Dublin: Irish Cattle Veterinary Association, 1986. "Vaccination for the prevention of bovine respiratory disease".
Cameron, C.M., et al; "Factors affecting the immunogenicity of *Pasteurella haaemolytica* in mice"; Ondertepoort J. Vet. Res., 51, 97–102 (1984).
Greer, C.M., et al; "*Pasteurella haemolytica* leucotoxin–tools for its investigation"; MSc Thesis, University of Guelph (1986).

(Continued)

*Primary Examiner*—Sharon L Turner

(57) ABSTRACT

A vaccine against Pasteurella comprising a proteinaceous material isolated from Pasteurella grown under iron-restricted conditions, but not from Pasteurella grown under normal conditions in vitro, which reacts in an immunoblotting test against the serum of a convalescent sheep or cow which has recovered from an infection by Pasteurella of the same serotype, together with an adjuvant.

OTHER PUBLICATIONS

Angen, O. et al. (1999) *Int. J. Syst. Bacteriol.* 49, 67–86. "Taxonomic relationships of the [*Pasteurella*] *haemolytica* complex as evaluated by DNA–DNA hybridizations and 16S rRNA sequencing with proposal of *Mannheima haemolytica* gen. nov., comb. nov., *Mannheimia granulomatis* comb. nov., *Mannheimia glucosida* sp. nov., *Mannheimia ruminalis* sp. nov. and *Mannheima varigena* sp. nov."

Bosworth, T.J. and Lovell, R., (1944), *J. Comp. Path.* 54, 168–171. "The occurrence of haemolytic cocco–bacilli in the nose of normal sheep and cattle".

Gauthier, G. et al, (1995), *Int. J. Syst. Bacteriol.* 45, 139–144. "Small–subunit and whole DNA relatedness concur for the reassignment of *Pasteurella piscicida* to the genus *Photobacterium* as *Photobacterium damsela* subsp. *piscicida* comb.nov."

Janssen, W.A. and Surgalla, M.J., (1968), *J. Bacteriol.* 96, 1606–1610. "Morphology, physiology, and serology of a *Pasteurella* species pathogenic for white perch".

Lovell, R. and Hughes, D.L., (1935), *J. Comp. Path.* 48, 267–284. "Diseases of young calves: a bacteriological examination of 100 cases".

Newsom, I.E. and Cross, F. (1932), *J. Am. Vet. Med. Assoc.* 80, 711–719. "Some bipolar organisms found in pneumonia in sheep".

Simidu, U. and Egusa, S., (1972), *Bull. Jpn. Soc. Sci. Fish* 38, 803–812. "A re–examination of the fish–pathogenic bacterium that had been reported as a *Pasteurella* species".

Skerman, V.B.D. et al, (1989), *Approved lists of bacterial names, amended edition,* p. 108–110, American Society of Microbiology, Washington DC.

Smith, G.R., (1961), *J. Path. Bact.* 81, 431–440. "The characteristics of two types of *Pasteurella haemolytica* associated with different pathological conditions in sheep".

The FreeDictionary by Farlex, Google Search. No date.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3, 6–13 and 15 is confirmed.

Claims 4–5 and 14 are cancelled.

New claims 16–18 are added and determined to be patentable.

*16. A vaccine comprising an effective amount of killed whole cells of Pasteurella haemolytica grown under iron-restriction conditions in vitro sufficient to induce an iron-restriction protein having a molecular weight of about 70,000 Daltons, together with an adjuvant.*

*17. The vaccine of claim 16 wherein said killed whole cells are in the form of a bacterin.*

*18. The vaccine of claim 16 wherein the said Pasteurella haemolytica is of serotype A2.*

* * * * *